United States Patent
Mantri et al.

(10) Patent No.: US 8,870,807 B2
(45) Date of Patent: Oct. 28, 2014

(54) GASTRO-INTESTINAL COMPRESSION DEVICE

(76) Inventors: Surag Mantri, Sunnyvale, CA (US);
Hoang Nguyen, San Jose, CA (US);
Niyazi Beyhan, Santa Clara, CA (US)

( * ) Notice: Subject to any disclaimer, the term of this patent is extended or adjusted under 35 U.S.C. 154(b) by 404 days.

(21) Appl. No.: 13/186,429

(22) Filed: Jul. 19, 2011

(65) Prior Publication Data
US 2012/0065651 A1    Mar. 15, 2012

Related U.S. Application Data

(60) Provisional application No. 61/365,774, filed on Jul. 19, 2010.

(51) Int. Cl.
*A61F 2/04* (2013.01)
*A61M 5/00* (2006.01)
*A61B 17/11* (2006.01)
*A61F 5/00* (2006.01)
*A61B 17/00* (2006.01)

(52) U.S. Cl.
CPC ... *A61B 17/1114* (2013.01); *A61B 2017/00818* (2013.01); *A61F 2002/045* (2013.01); *A61F 2002/044* (2013.01); *A61B 2017/1132* (2013.01); *A61F 5/0076* (2013.01)
USPC ............................................. 604/8; 604/264

(58) Field of Classification Search
USPC .................. 604/8–9, 19, 264–284; 623/23.64–23.67, 24; 606/108, 151, 606/153–154, 215
See application file for complete search history.

(56) References Cited

U.S. PATENT DOCUMENTS

| | | | |
|---|---|---|---|
| 7,025,791 B2 | 4/2006 | Levine et al. | |
| 2005/0049718 A1* | 3/2005 | Dann et al. | 623/23.65 |
| 2005/0125075 A1* | 6/2005 | Meade et al. | 623/23.64 |
| 2008/0195226 A1* | 8/2008 | Williams et al. | 623/23.67 |

OTHER PUBLICATIONS

Cummings, E. David, Overduin, Joost, Foster-Schubert, and Karen E. "Gastric Bypass for Obesity: Mechanisms of Weight Loss and Diabetes Resolution" Clinical Endocrinology and Metabolism, vol. 89 (6), pp. 2608-2615.

* cited by examiner

*Primary Examiner* — Tatyana Zalukaeva
*Assistant Examiner* — Benedict L Hanrahan
(74) *Attorney, Agent, or Firm* — Convergence Intellectual Property Law P.C.

(57) ABSTRACT

Devices, methods, and systems for treating Type-2 Diabetes and/or obesity by facilitating the delivery of under-digested nutrients within the gastro-intestinal tract without substantial tissue removal are disclosed. In one aspect, the gastro-intestinal tract of a patient is modified by a gastro-intestinal treatment device comprising an elongate element configured to extend within the gastro-intestinal tract, a first attachment element and a second attachment element disposed on the elongate element, wherein the first attachment element and the second attachment element are configured to attach to the gastro-intestinal tract such that a portion of the gastro-intestinal tract is compressed between the first and the second attachment elements. The length of the gastro-intestinal tract modified by the device is effectively shortened, and its surface area is reduced.

17 Claims, 12 Drawing Sheets

GASTRO-INTESTINAL COMPRESSION DEVICE

CROSS-REFERENCES TO RELATED APPLICATIONS

This application claims the benefit and priority of U.S. Provisional Application No. 61/365,774, filed on Jul. 19, 2010, the full disclosure of the above referenced application is incorporated herein by reference.

BACKGROUND

1. Field of Invention

The present embodiments relate generally to treating Type-2 Diabetes, obesity, and aid in weight loss by facilitating the delivery of under-digested nutrients within the gastro-intestinal tract without substantial tissue removal.

2. Description of the Related Art

Diabetes mellitus Type-2 is a metabolic disorder that is characterized by high blood glucose in the context of insulin resistance and relative insulin deficiency. There are an estimated 17.9 million people in the United States diagnosed with Diabetes, 90% of whom are Type-2.

Recently, it has been observed that gastric bypass procedures such as the Roux-en-Y Gastric Bypass (RYGB) employed to treat morbid obesity result in amelioration of Type-2 Diabetes. In five published studies summarized by Cummings, E. David, Overduin, Joost, Foster-Schubert, and Karen E. in *Gastric Bypass for Obesity: Mechanisms of Weight Loss and Diabetes Resolution* published in the Journal of Clinical Endocrinology and Metabolism 89 (6):2608-2615, a total of 3,568 diabetic patients undergoing RYGB, were examined and 82-98% of patients enjoyed complete remission of their disease, with most studies showing resolution in approximately 83% of cases. The reversal of impaired glucose tolerance without Diabetes was nearly universal. Patients whose Diabetes remitted were able to discontinue all diabetic medications and manifest normal fasting glucose and glycosylated hemoglobin levels.

Thus, gastric bypass procedure is a highly effective method to reverse Diabetes, which is traditionally regarded as a progressive, unrelenting disease. The most obvious mechanism to explain this effect is the beneficial impact of weight loss on insulin sensitivity. Indeed, patients who have lost substantial weight after RYGB display increased levels of adiponectin (which increases insulin sensitivity) and muscle insulin-receptor concentration, as well as reductions in intramuscular lipids and fatty acyl-coenzyme A molecules (moieties that cause insulin resistance). As predicted, insulin sensitivity increased approximately 4 to 5-fold after RYGB-induced weight loss.

The beneficial effects of RYGB on Type-2 Diabetes, however, cannot be accounted for by weight loss alone. Perhaps the most impressive observation is that previously diabetic patients typically discontinue all of their Diabetes-related medications at the time of discharge from the hospital after RYGB, long before major weight loss has occurred.

A proposed hypothesis for the anti-diabetic phenomenon is that gastric bypass procedures expedite delivery of under-digested nutrients to the hindgut. The presence of under-digested nutrients in the ileum suppresses gastrointestinal motility, gastric emptying, small intestinal transit, and thus, food intake. Neural mechanisms are implicated in this response, as well as hormones, including PYY, glucagon-like peptide-1 (glp-1), neurotensin, and enteroglucagon. Particularly, enhanced glp-1 secretion from facilitated delivery of nutrients to the hindgut may result in increased glucose tolerance and may account for anti-diabetic effects of gastric bypass procedures.

However, gastric bypass procedures are highly invasive and can carry a heavy toll. For example, morbidity rate is high with 11% requiring surgical intervention for correction. Additionally, post-treatment small bowel obstruction occurs at a rate between 2-6% and mortality rates are reported to be ~0.5-1.5%. While surgery seems to be an effective answer, the high complication rates make the current procedures impractical for most patients. Furthermore, although laparoscopic techniques provide fewer surgical complications, patients are still exposed to high operative risk in addition to requiring an enormous level of skill by the surgeon.

Sleeve gastrectomy procedures and devices such as that disclosed in U.S. Pat. No. 7,025,791 have been proposed to sleeve or cover a portion of the gastro-intestinal tract to achieve similar results as the more invasive surgical procedures. However, one drawback of these devices is that nutrients travel at the normal rate if not slower to the distal portion of the small intestine, thus such devices may not promote glp-1 secretion. Furthermore, the distal sleeve of these devices may not be patent and thus contribute to more resistance.

To remedy the shortcomings, it would be desirable to provide novel methods, devices or systems that expedite the delivery of under-digested nutrients to the hindgut to treat Type-2 Diabetes, obesity, or facilitate weight lost without tissue removal. Additionally, it would be desirable for such methods and devices to be non-invasive such that treatment complications are minimized. Furthermore, it would be desirable for such methods and devices to achieve long-term benefits to the subject even after the removal of the device. At least some of these objectives will be met by the embodiments described below.

SUMMARY

Devices, methods and systems for treating Type-2 Diabetes and/or obesity by facilitating the delivery of under-digested nutrients within the gastro-intestinal tract without substantial tissue removal are disclosed.

In one aspect, a gastro-intestinal treatment device configured to modify a portion of the gastro-intestinal tract comprising an elongate element configured to extend within the gastro-intestinal tract, a first attachment element disposed on the proximal end of the elongate element, and a second attachment element disposed on the elongate element, wherein the first attachment element and the second attachment element are configured to attach to the gastro-intestinal tract such that a portion of the gastro-intestinal tract is compressed between the first and the second attachment elements. The length of the gastro-intestinal tract modified by the device is effectively shortened, and/or its surface area is reduced. It is further contemplated that an embodiment of the present device may comprise a third attachment element configured to attach to the gastro-intestinal tract.

In one aspect, the device is configured to maintain the compression of the portion of the gastro-intestinal tract between the first and the second attachment elements for a period of time.

In another aspect, the elongate element of the device is configured to at least partially cover the compressed portion of the gastrointestinal tract such that the under-digested nutrients passing through the compressed portion do not substantially come into contact with the gastrointestinal tissue. The elongate element may comprise an inner layer constructed of biocompatible low friction material. The elongate element may also comprise an outer layer constructed of compliant material.

In one aspect, at least one of the attachment elements comprises at least one anchoring mechanism. The anchoring mechanisms may be self expanding such as a radial stent, mechanical fasteners, or chemical fasteners.

In one aspect, the device may further comprise a tension element such as a spring, a braid, or a net disposed within the elongate element.

In one aspect, the device may comprise one or more openings disposed on the surface of the elongate element such that the under-digested nutrients may be in partial contact with the gastro-intestinal tissue. Furthermore, the device may comprise an adjustment element configured to adjust a degree of compression.

In another aspect, a device may be implanted within the gastrointestinal tract comprising an elongate element extending within a portion of the gastro-intestinal tract, a first attachment element, and a second attachment element disposed on both ends of the elongate element. The attachment elements are each configured to attach to a portion of the gastro-intestinal tract such that the device is implanted or localized within the gastro-intestinal tract.

In yet another aspect, the device further contemplates a tissue modification device comprising an elongate element configured to extend within a body region, a first attachment element disposed on the proximal end of the elongate element, and a second attachment element disposed on the distal end of the elongate element. The first and the second attachment elements are configured to attach to the body region such that a tissue portion is compressed and remodeled between the first and the second attachment elements. The tissue modified by the device may be gastro-intestinal tissue, or any other tissue.

In one aspect, the device is configured to remodel or modify the tissue portion permanently. In such embodiment, the device may be constructed of bioabsorbable material.

In another aspect, the device is constructed of transparent or translucent materials to enable visual monitoring of the treatment region.

The present disclosure further contemplate increasing or decreasing the diameter of the gastro-intestinal tract to increase the passage of the under-digested nutrients or to reduce the effective surface area of the gastro-intestinal tract.

The present disclosure also contemplates a method of compressing a portion of the gastro-intestinal tract comprising the steps of attaching a first attachment element to the gastro-intestinal tract, compressing a portion of the gastro-intestinal tract, and attaching a second attachment element to the gastro-intestinal tract. Additionally, the present disclosure contemplates compressing a portion of the gastro-intestinal tract and maintaining the compressed portion for a period of time.

This, and further aspect of the present disclosure, are set forth herein.

BRIEF DESCRIPTION OF THE DRAWINGS

The invention has other advantages and features which will be more readily apparent from the following detailed description of the invention and the appended claims, when taken in conjunction with the accompanying drawings, in which:

FIGS. 2A-3C illustrate steps of an exemplary operation of the present tissue compression device.

DETAILED DESCRIPTION

Although the detailed description contains many specifics, these should not be construed as limiting the scope of the disclosure but merely as illustrating different examples and aspects of the disclosure. It should be appreciated that the scope of the disclosure includes other embodiments not discussed in detail herein. Various other modifications, changes and variations which will be apparent to those skilled in the art may be made in the arrangement, operation and details of the method and apparatus disclosed herein without departing from the spirit and scope of the disclosure as described here.

The present disclosure relates to devices, methods, and systems configured to shorten the gastro-intestinal tract and reduce gastro-intestinal functional area without removing gastro-intestinal tissue. Specifically, embodiments of the present disclosure relate to minimally invasive devices, methods, and systems to treat Type-2 Diabetes and/or obesity without the need for surgery by compressing and/or covering a portion of the gastrointestinal tract and maintaining the compressed configuration for a period of time.

It has been observed that Type-2 Diabetes may be controlled by more rapid delivery of nutrients from the stomach to the distal small intestine, thereby enhancing the release of hormones such as glucagon-like peptide-1 (glp-1). In addition, exclusion of the under-digested nutrients from a portion of the proximal small intestine reduces or suppresses the secretion of anti-incretin hormones, which leads to improvement of blood glucose control.

The present embodiments effectively reduce the length and the functional surface area of a portion of the gastro-intestinal tract such as the foregut and allow under-digested nutrients to travel more quickly into the more functional portion such as the hindgut. Specifically, the present embodiments are configured to compress and optionally cover a portion of the gastro-intestinal tract, for example, a portion of the proximal small intestine, such that the exposure of under-digested nutrients to intestinal tissue is not only decreased but also the rate at which under-digested nutrients travel to the functional tissue is increased.

While embodiments of the present disclosure described herein are specifically directed at treating and modifying the gastro-intestinal tract, certain aspects of the disclosure may also be used to treat and modify other tissues, organs, or body lumens such as the lung airways, heart, vascular structures (arteries & veins), kidneys, reproductive system (fallopian tubes), etc.

Figure 1:
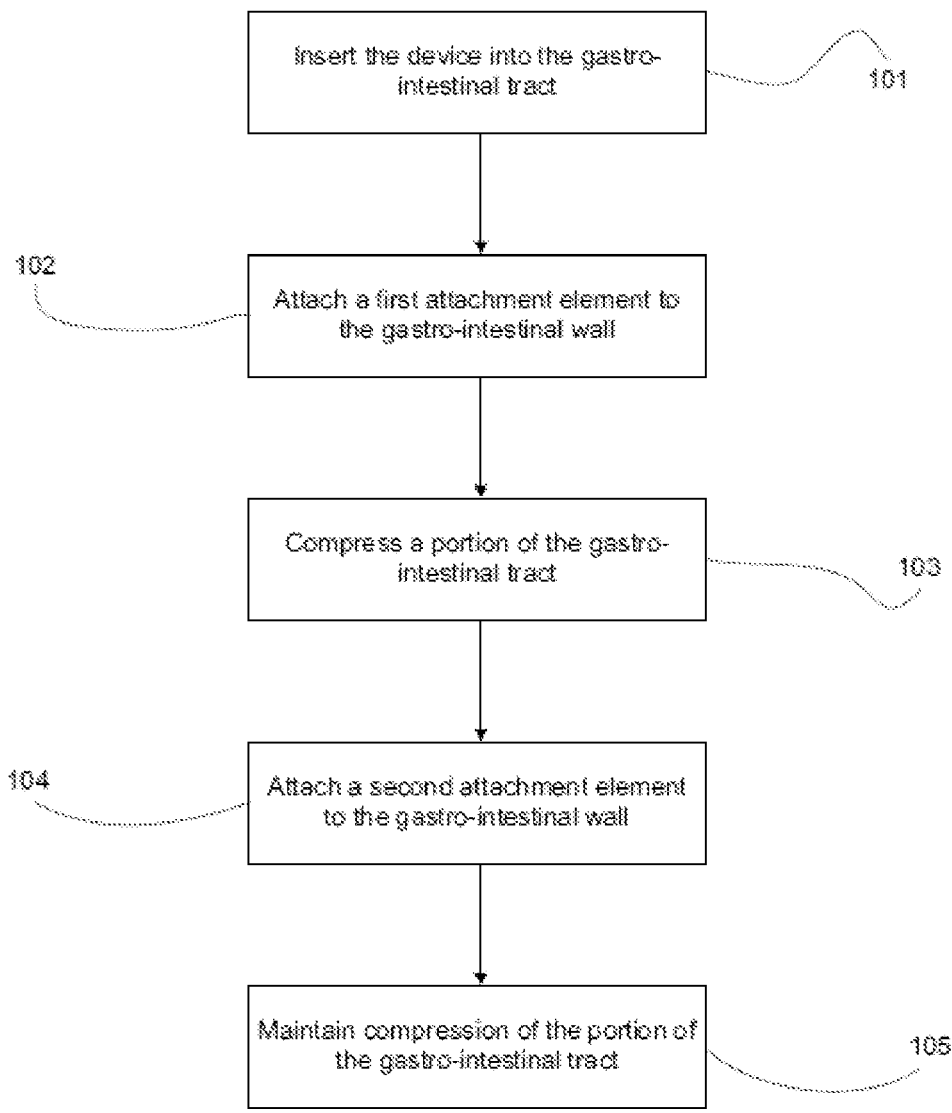
FIG. 1 is a flow diagram illustrating an exemplary operation of the present tissue compression device.
Figure 2A:
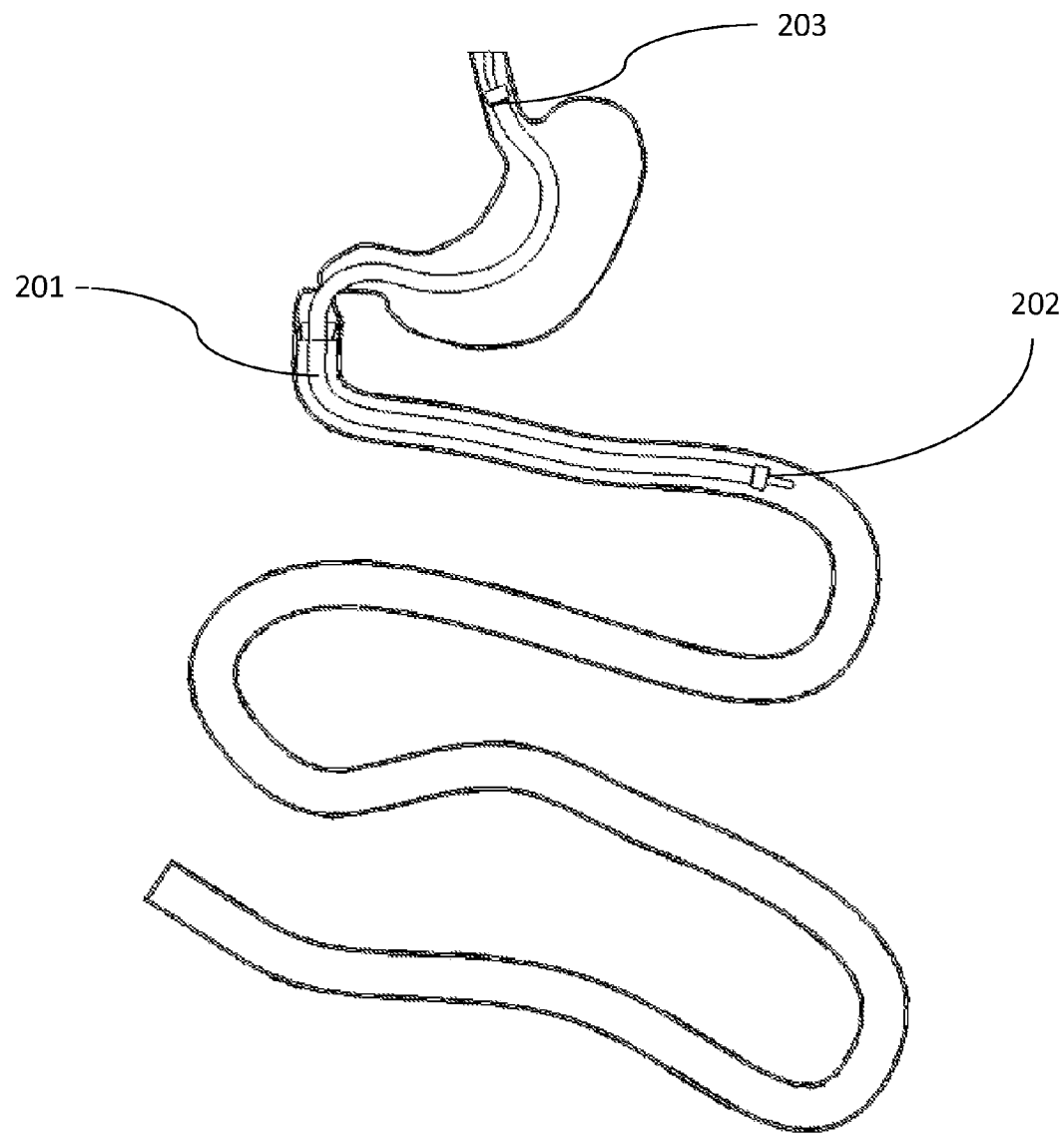
Figure 2B:
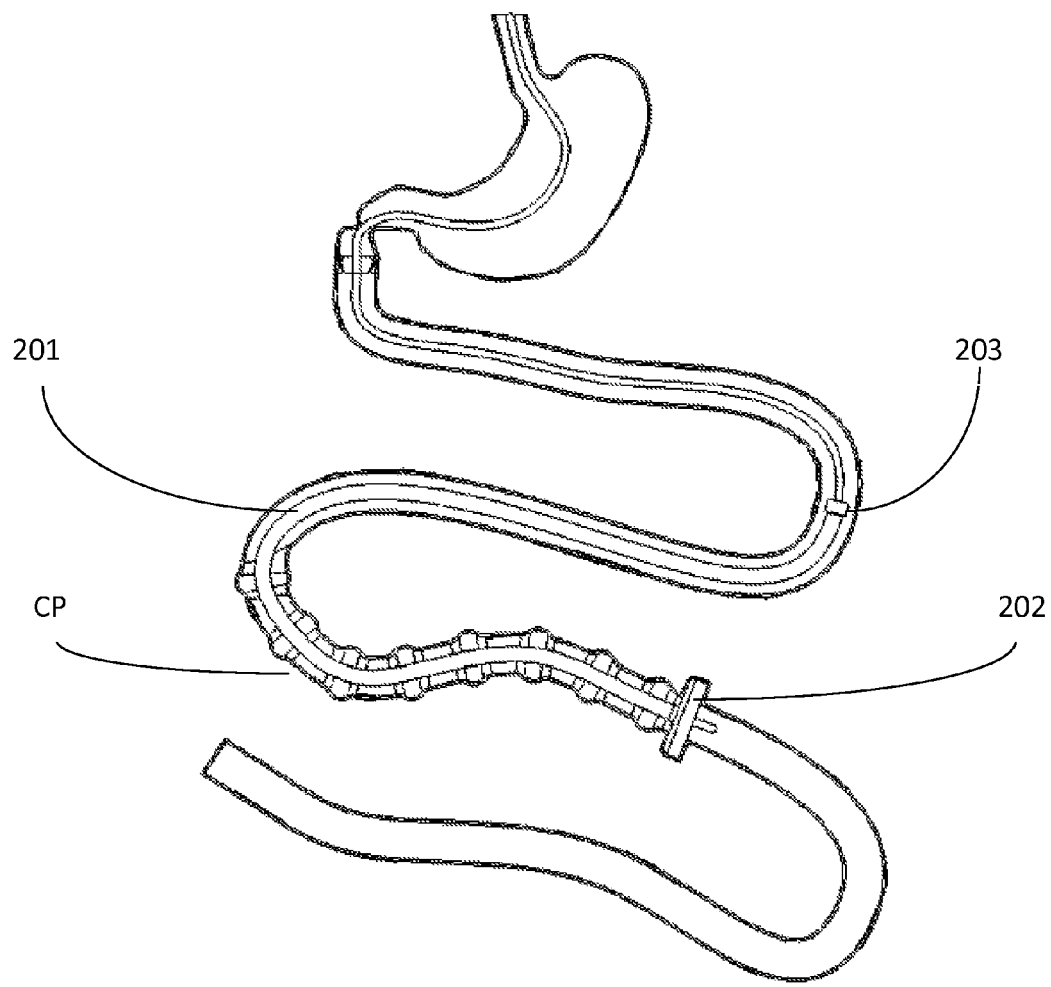
Figure 2C:
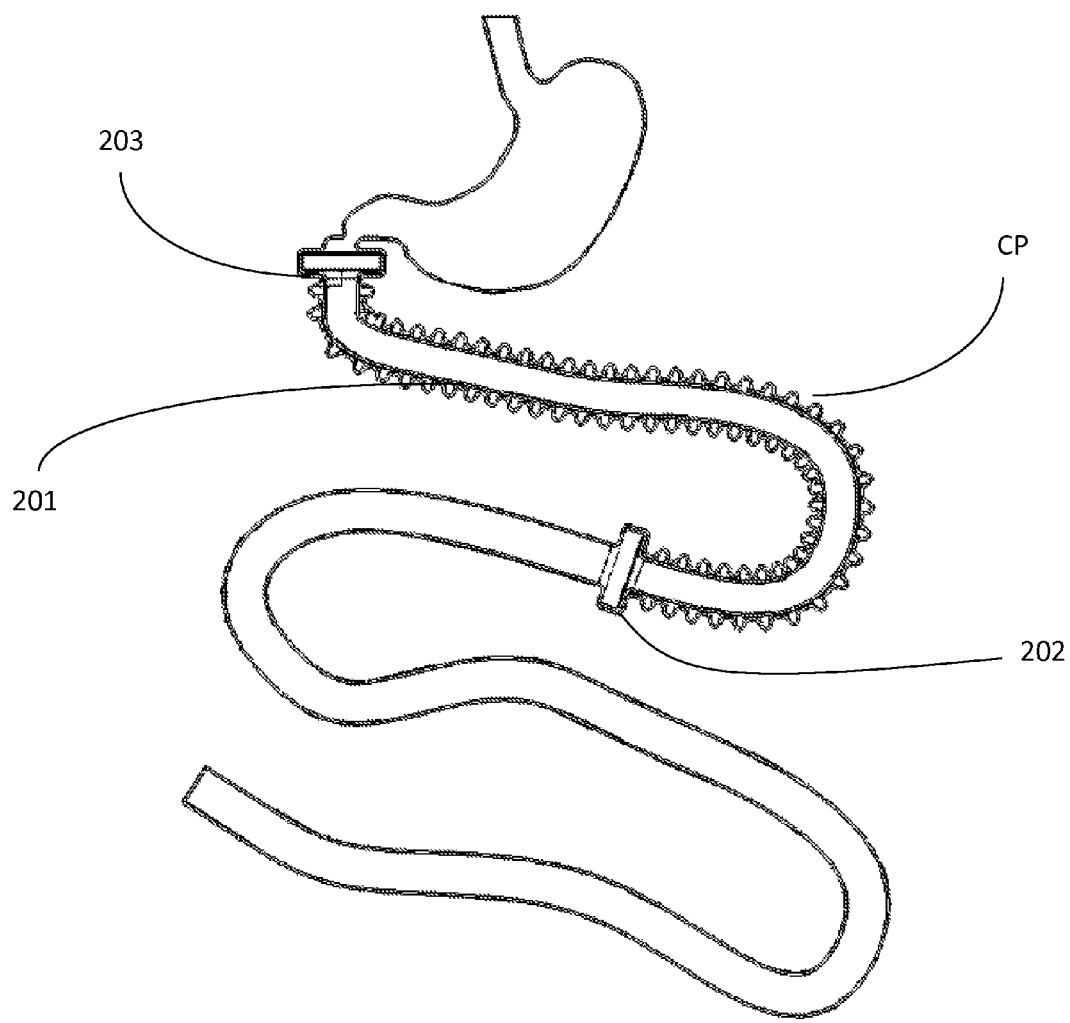

Referring now to FIG. 1, which is a flow diagram illustrating an exemplary operation of the present device, which is also schematically illustrated in FIGS. 2A-2C. At step 101 and as seen in FIG. 2A, one embodiment of the compression device comprises a first attachment element 202, a second attachment element 203, and an elongate element 201 disposed in-between is inserted endoluminally using a delivery catheter into a natural lumen of the gastro-intestinal tract. At step 102 and as seen in FIG. 2B, the first attachment element 202 of the device is attached to a first attachment site by engaging with the gastro-intestinal wall. At step 103, a portion of the gastro-intestinal tract is modified by compressing a portion of the gastro-intestinal tract between the first and the second attachment elements such that a second attachment element 203 is aligned with a second attachment site. In one embodiment, the compression is accomplished by mechanically pulling the device in the proximal direction such that the second attachment element 203 is aligned with the second attachment site. Alternatively, the compression may be accomplished by any other methods known in the art. For example, it is contemplated that a portion of the gastro-intestinal tract may be compressed before the insertion of the device. Alternatively, the first and the second attachment elements may both be attached to the gastro-intestinal wall prior to compression.

At step 104 and as seen in FIG. 2C, the second attachment element 203 is attached to the second attachment site by engaging the second attachment element 203 with the gastro-intestinal wall. After both attachment elements are attached to their respective attachment sites, at step 105, the compressed portion CP of the gastro-intestinal tract is maintained and the length and the surface area of the gastro-intestinal tract is effectively reduced for at least a period of time.

Optionally, the compressed portion of the gastro-intestinal tract CP is covered or sleeved by the elongate element 201 such that under-digested nutrients in the compressed portion of the gastro-intestinal tract CP are substantially isolated from the gastro-intestinal tissue.

As seen in FIGS. 2A-2C, the first attachment element 202 may be attached to a distal first attachment site, and the first attachment element 202 is then retracted towards the proximal direction to compress the gastrointestinal tract. The second attachment element 203 proximal to the first attachment element 202 is then attached to a proximal second attachment site to maintain the compressed portion of the gastro-intestinal tract.

Alternatively, the first attachment element 202 may be attached to a proximal first attachment site, and the gastro-intestinal tract is then retracted distally towards the first attachment element 202. The second attachment element 203 distal to the first attachment element 202 is then deployed at the distal second attachment site to maintain the compressed portion of the gastro-intestinal tract.

Furthermore, it is envisioned that the attachment elements may be deployed within the gastro-intestinal tract without modifying the gastro-intestinal tract. In such embodiment, the attachment elements may be used to stabilize the elongate element within the gastro-intestinal tract to cover or isolate a portion of the gastro-intestinal tissue from the under-digested nutrients.

A shortened gastro-intestinal tract is advantageous since under-digested nutrients passing through the gastrointestinal tract can be more rapidly delivered to the distal small intestine, thereby enhancing the release of hormones such as glp-1. Furthermore, by reducing the functional surface area through compression and/or coverage, the secretion of anti-incretin hormones may be reduced or suppressed. The combined results of compressing and covering a portion the gastrointestinal tract by an embodiment of the present device may therefore lead to weight loss and improvement of blood glucose control and thereby serve as a treatment for Type-2 Diabetes.

In another embodiment, the present device is configured to be implantable such that the device may be implanted in a patient for an extended period of time. In one embodiment, the device is configured to be permanently implanted within the patient without the need of removal. In such embodiment, the device may be configured to be biodegradable or bioabsorable. In another embodiment, the device is configured to be removable after a treatment period.

Figure 3A:
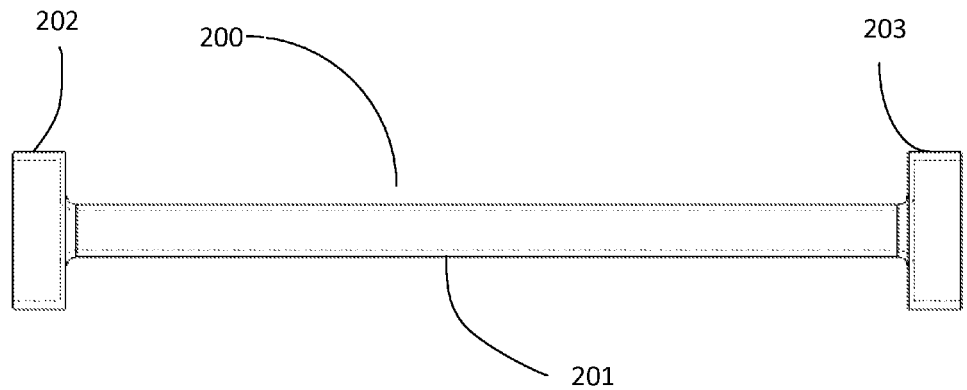
FIGS. 3A-3B illustrate schematics of an exemplary gastro-intestinal compression device.
Figure 3B:
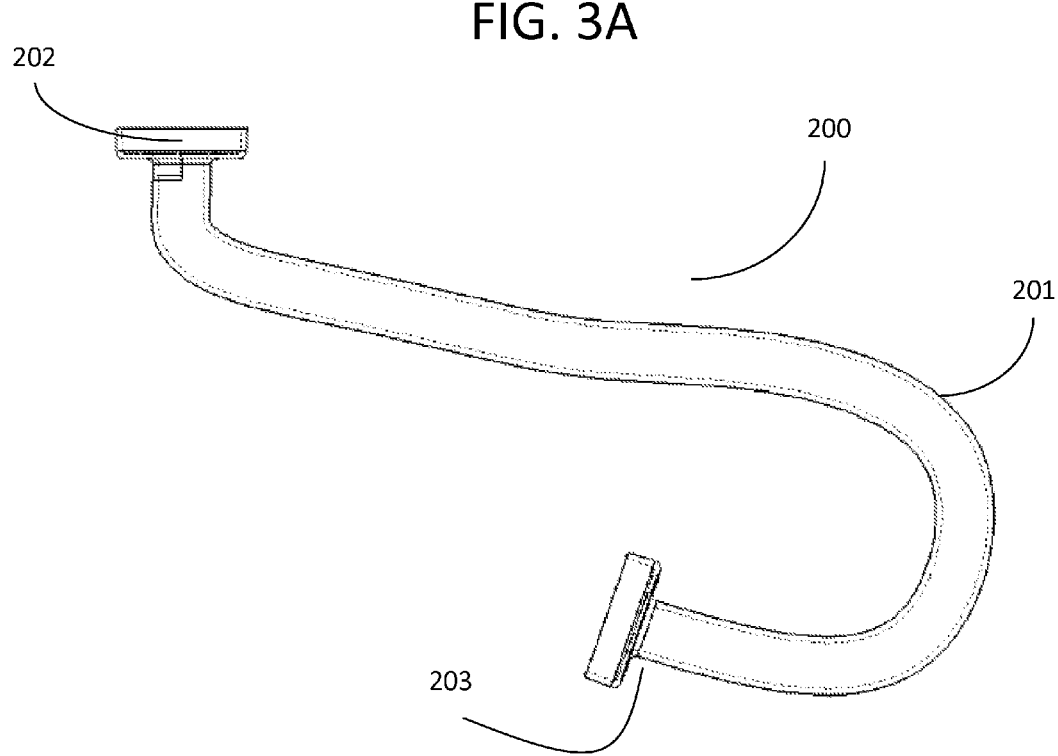

Referring now to FIGS. 3A and 3B, where schematics of an exemplary device constructed in accordance with the principles of the present invention are shown. The device 200 is configured for insertion within a natural lumen of a gastro-intestinal tract comprising a first attachment element 202, a second attachment element 203 and an elongate element 201 disposed in-between the attachment elements. Alternatively, the attachment elements may be disposed along the elongate element.

The first attachment element 202 is configured to attach to a first attachment site such as a portion of the duodenum just distal to the pylorus and the second attachment element 203 is configured to attach to a second attachment site that is distal to the first attachment site. In one embodiment, the elongate element 201 comprises an open ended tubular body, wherein the tubular body defines a substantially hollow space with a distal opening and a proximal opening. The under-digested nutrients enter the elongate element 201 through the proximal opening and pass through the tubular body and exit the device through the distal opening substantially unobstructed. In one embodiment, the distal and the proximal openings are substantially defined by the first and the second attachment elements.

The elongate element 201 may be supported such that the elongate element 201 is configured to maintain a predetermined volume within the body of the elongate element 201. Alternatively and optionally, the elongate element 201 may be constructed in a shape that substantially conforms to the natural shape or contort of the portion of the gastro-intestinal tract where the device is configured to be inserted. For example, the elongate element 201 may be shaped to conform to the shape and contort of a portion of the duodenum.

In another embodiment, the elongate element 201 may be unsupported, such as an elastic sleeve. The unsupported configuration may be advantageous by substantially minimizing interference or resistance with the peristaltic motion of the gastro-intestinal tract and thus reduce irritation or other complications.

In the unsupported embodiment, the device 200 may further comprise a rigid element (not shown) disposed within the elongate element 201 configured to maintain compression. In one embodiment, the rigid element may comprise a rod connected to the attachment elements such that the rigid element is substantially suspended within the elongate element 201. Optionally, the rigid element may be adjustable such that the degree of compression may be adjusted according to subject's anatomy and/or treatment requirements.

It is further contemplated that a portion of the elongate element is supported and another portion is unsupported. For example, in one embodiment, the portion of the elongate element that is in contact with the attachment elements may be supported and the other portion of the elongate element is unsupported.

Generally, the elongate element 201 has material properties that are selected to minimally irritate the gastro-intestinal tract. In one embodiment, the elongate element 201 can be formed of substantially elastic materials such as urethane, silicone, or a combination thereof. In another embodiment, the elongate element 201 can be formed of substantially rigid materials such as fluoropolymers and/or polyolefin. Examples of fluoropolymers that may be used to construct the elongate element 201 includes PolyTetraFluoroThylene (PTFE), expanded PTEF (ePTFE), Fluorinated Ethylene Propylene (FEP), PerFluoroAlkoy (PFA), Ethylene TetraFluoro-Ethylene (ETFE), etc. Examples of polyolefins include polyethylene and polypropylene. It is further contemplated that the elongate element 201 may form of any biocompatible materials, or any combination thereof.

Alternatively, the elongate element 201 may be a telescoping element comprising at least two telescoping portions such that the elongate element may be extended or contracted by sliding or moving the telescoping portions. In such embodiments, the elongate element 201 further comprises at least one locking element configured to lock the telescoping portions such that the elongate element 201 maintains a desired length.

Figures 4A, 4B:
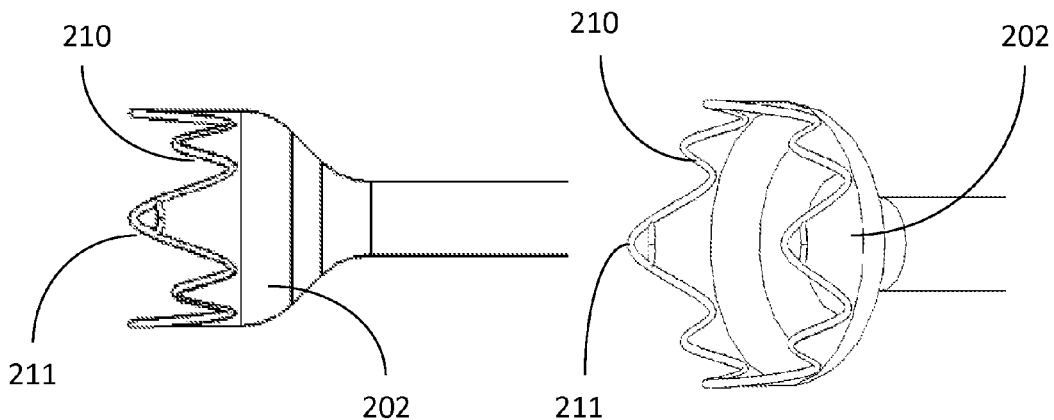
FIGS. 4A-4D illustrate various exemplary attachment elements.

The attachment elements each comprise one or more anchoring mechanisms configured to attach and stabilize the attachment elements within the gastro-intestinal tract. In one embodiment, the anchoring mechanisms are self-expanding stents such as metal or plastic radial stents. As seen in FIGS. 4A-4B, an attachment element 202 comprises a self-expanding ring 210 disposed on the outer surface or outer edge of the attachment element is exemplarily shown. The self-expanding ring 210 may be constructed of Nickel Titanium alloy (Nitnol) or other biocompatible material with shape memory properties. The attachment element 202 comprising the self-expanding ring 210 is configured to be inserted into the gastro-intestinal tract in the substantially compressed configuration. Upon insertion, the self-expanding ring 210 is configured to expand within the gastro-intestinal tract, where the expansion of the self-expanding ring 210 causes the attachment element 202 to engage and substantially securely attach to the gastro-intestinal wall. In one embodiment, the self-expanding ring 210 comprises one or more protrusions 211 configured to prevent the attachment element 202 from migrating, slipping and/or otherwise deviating from the attachment site once the attachment element has engaged with the gastro-intestinal wall.

Alternatively, the anchoring mechanisms may be one or more mechanical fasteners such as sutures, surgical staples, or barbs. In another embodiment, the anchoring mechanism is a chemical fastener such as adhesive or fibrinogen.

Figures 4C, 4D:
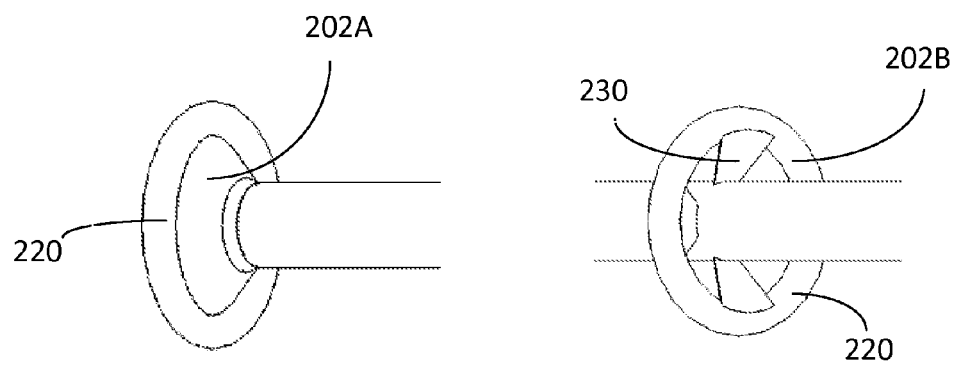

In yet another embodiment, the anchoring mechanism is a balloon such as a fluid-filled balloon, gas-filled balloon, or non-elastic balloon. In such embodiment, the attachment elements may be configured to comprise one or more inflatable elements as illustrated in FIGS. 4C-4D. As seen FIG. 4C, the attachment element 202A comprises an inflatable element 220 disposed on the outer surface or outer edge of the attachment element 202A. The inflatable element 220 may be configured as a fluid-filled balloon, whereupon injection of an inflation fluid, the volume or a surface area of the inflatable element 220 is expanded. It is contemplated that the inflation fluid may be a biocompatible gas or liquid that is delivered to the inflatable element 220 through an inflation port (not shown). The inflatable element 220 may assume various configurations that enable the inflatable element 220 to engage and attach to the gastro-intestinal wall. For example, the inflatable element 220 may assume a tire-like configuration disposed on the outer edge of the attachment element 202A as seen in FIG. 4C.

In one embodiment, the anchoring element 202A comprising an inflatable element 220 is inserted into the gastro-intestinal tract in a substantially deflated configuration. Upon insertion, an inflation fluid is delivered to the inflatable element 220. Whereupon receiving the inflation fluid, the inflatable element 220 is configured to expand within the gastro-intestinal tract. The inflatable element 220 is configured to expand within the gastro-intestinal tract such that a portion of the anchoring element 202A engages and/or substantially securely attaches to the gastro-intestinal wall.

In another embodiment, as seen in FIG. 4D, the attachment element 202B comprises at least one supporting element 230 that is configured to support the inflatable element 220. In such embodiment, the supporting element 230 is configured to provide support for the inflatable element 220 and to support the engagement and attachment of the attachment element 202B to the gastro-intestinal wall. The support element 230 may be configured to counteract against any inward force as exerted by the gastro-intestinal tract. In yet another embodiment, the entire anchoring element may be inflatable.

In one embodiment, the first and second attachment elements are configured as substantially cylindrical structures. In such embodiment, each of the attachment elements comprises a body that defines an opening within the body. The anchoring mechanisms as described above may be disposed on a surface of the body. The opening, where the under-digested nutrients enter the device or where the under-digested nutrient exit the device, may be defined by the body of the attachment element. The opening may be substantially circular, oval, or it may be of any arbitrary shape or configuration.

The attachment elements are configured to withstand the radial force imparted by the gastro-intestinal tract. Additionally, the attachment elements may be configured to be atrumatic by providing flexibility and compliance such that the likelihood of tissue erosion or damage is minimized. The compliance of the attachment elements may be configured by varying at least one or the material, shape, and/or dimensions to accommodate different patients. Furthermore, the attachment elements may be adjustable such that the shape and/or dimensions of the attachment elements may be configured or reconfigured during and/or after the insertion procedure.

The attachment elements including the anchoring mechanisms may be made from any biologically compatible resilient material. For example, the material can be metal, an alloy, a plastic or combinations of these materials. In one embodiment, the attachment elements are made of stainless steel. In another embodiment, the attachment elements are made of super-elastic alloy such as Nitnol.

The first and second attachment elements as described above may be substantially similar. Alternatively, the first and second attachment elements may be different such that the type and/or number of anchoring mechanisms, material, shape, or structure of the proximal attachment element may be different from that of the distal attachment element or vice versa.

Figure 5:
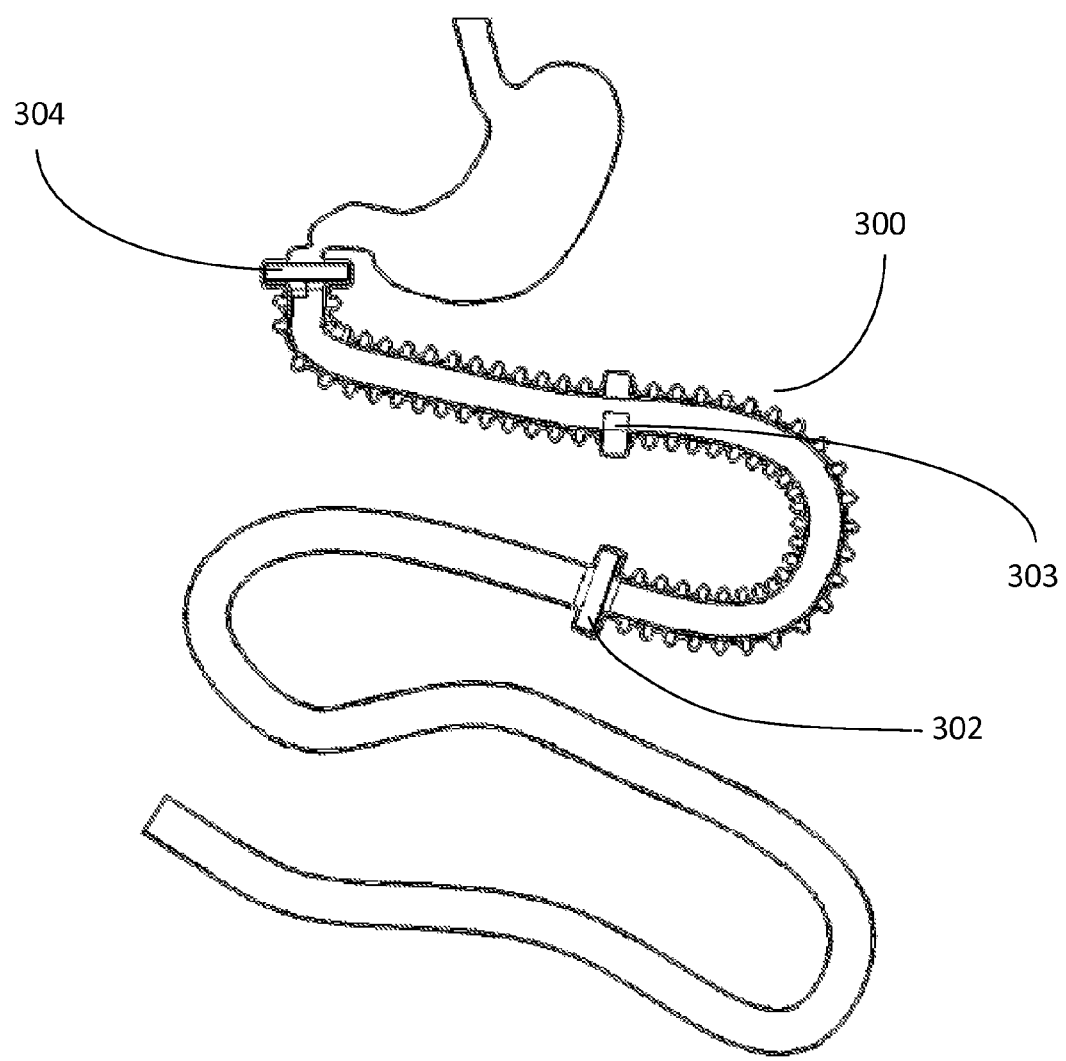
FIG. 5 illustrates an exemplary device with three attachment elements.

It is contemplated that the present device may comprise more than two attachment elements, as exemplarily shown in FIG. 5. As seen in FIG. 5, the device 300 comprises a first attachment element 302, a second attachment element 303, and a third attachment element 304 disposed along an elongate element 301. Although the device 300 is exemplarily shown with three attachment elements, it is contemplated that the device may comprise any number of attachment elements.

An embodiment with more than two attachment elements may be advantageous in that the device 300 may effectively adapt to bends in the anatomy of the gastro-intestinal tract.

Additionally, having more than two attachment elements may create attachment redundancy which may prevent migration and/or loss of compression. Furthermore, an embodiment with more than two attachment elements may potentially reduce pain to patient by distribution of radial force along the elongate element.

Furthermore, the device 200 may optionally comprise an adjustment element (not shown) configured to adjust the degree of compression and thereby adjust the length of the gastro-intestinal tract. By adjusting the degree of compression, it enables treatment to occur over a longer period time rather than acutely. Furthermore, by adjusting the degree of compression, long-term treatment schemes can be developed. For example, a patient may be treated with the present invention by reducing the length of the gastro-intestinal tract by 3% during the first phase of the treatment. In the second phase of the treatment, the length may be reduced by 2% by relaxing the degree of compression as the patient's condition improves. The adjustment element may be a mechanical device, a micro-motor, heat-sink element, liquid removal mechanism, threaded rod, etc.

Figure 6:
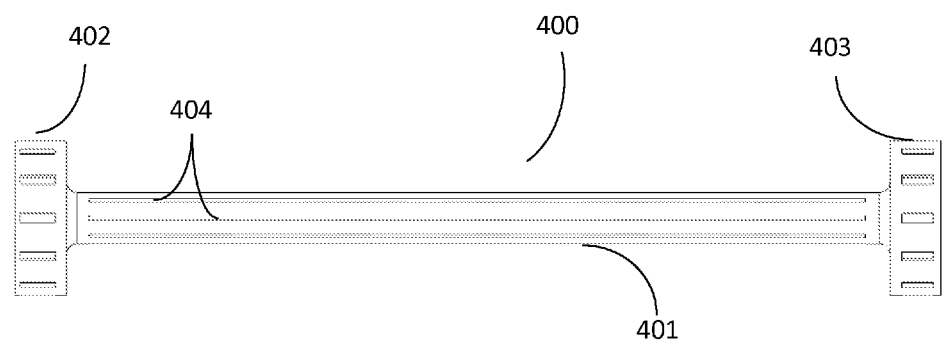
FIG. 6 illustrates one embodiment of the compression device incorporating an open sleeve design.

Referring now to FIG. 6, where an embodiment of the present disclosure comprising one or more openings disposed on the elongate element is exemplarily shown. As seen in FIG. 5, the device 400 comprises one or more openings 404 disposed on the elongate element 401, the first attachment element 402, and/or the second attachment element 403. The openings 404 may be permeable pores, valves, slits, etc. The openings 404 enable partial contact between the under-digested nutrients and a portion of the gastro-intestinal tract that is covered by the present device. The openings 404 allow the duodenum's digestive juices to enter the device to allow for partial or complete breakdown of the under-digested nutrients to prevent drastic physiological change to the modified portion of the gastro-intestinal tract.

Additionally, the openings 404 may be advantageous since bypassing the duodenum increases the difficulty for the body to digest fats, complex sugars, and/or carbohydrate rich foods. When carbohydrates directly enter the jejunum without first being conditioned in the duodenum, dumping syndrome occurs where the patient begins to feel lightheaded and experiences severe diarrhea.

The dumping syndrome may be desirable in certain treatment schemes in that it decreases fat absorption, and encourage behavioral modifications such that patients may decrease or eliminate fat or carbohydrate rich food from their diets to avoid the adverse side-effects. However, the severity of the dumping syndrome may causes significant discomfort and may be harmful to the patients. By allowing partial contact of the under-digested nutrients to the duodenum through the openings 404, the adverse side effect may be reduced. Furthermore, the present invention contemplates varying the location, size and/or number of the openings 404 disposed on the device 400 such that the amount of intestinal juices entering the device may be controlled. Additionally, it is contemplated that the size of the openings 404 may be adjustable to control the amount intestinal juices entering the device before or after the device has been inserted into the subject.

Figure 7:
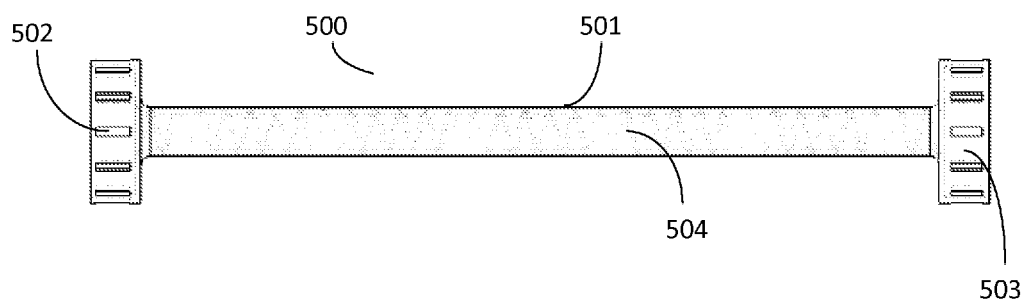
FIG. 7 illustrates one embodiment of the compression device incorporating a tension element.

Referring now to FIG. 7, where an embodiment of the present invention comprising at least one tension element is exemplarily shown. The device comprising at least one tension element is advantageous since it enables compression and reduction of gastro-intestinal length and area to occur over a longer period time rather than acutely, which may result in fewer traumas to the patient. It also allows for more precise control over the compression force along the gastro-intestinal tract, thereby preventing over-compression or under-compression.

As seen in FIG. 7, the device 500 comprises an elongate element 501, a first attachment element 502, a second attachment element 503, and a tension element 504 disposed in-between. In one embodiment, the tension element 504 is a spring, braid, or a net. In another embodiment, the tension element 504 is one or more bands disposed around the elongate element 501 with elastic characteristics. Alternatively, the tension element 504 may be any other device or apparatus that creates or maintains tension within at least a portion of the elongate element 401.

Figure 8:
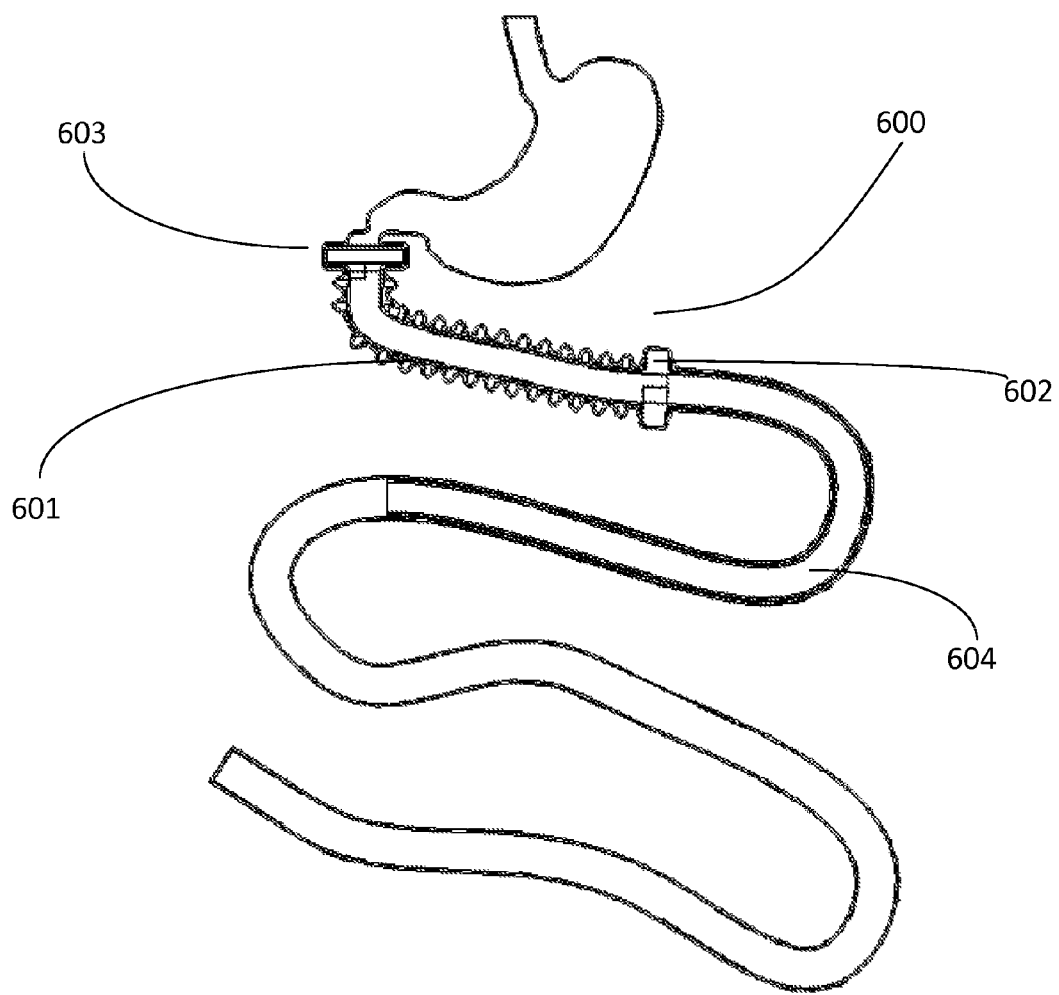
FIG. 8 illustrates one embodiment of the device comprising a covering element.

Referring now to FIG. 8, where an embodiment of the present disclosure comprising a covering element is exemplarily shown. As seen in FIG. 8, the device 600 comprises an elongate element 601, a first attachment element 602, a second attachment element 603, and a covering element 604. The first and the second attachment elements are configured to attach to the gastro-intestinal tract, and the elongate element 601 is configured to maintain a modified configuration of the gastro-intestinal tract as described above. The covering element 604 is configured to contact the under-digested nutrients traveling through the device 600.

As see in FIG. 8, the covering element 604 may be longer than the elongate element 601, such that the covering element 604 is partly disposed within the elongate element 601, and partly disposed within the unmodified portion of the gastro-intestinal tract. In such embodiment, additional portion of the gastro-intestinal tract may be covered to substantially prevent or limit contact between the under-digested nutrients and the gastro-intestinal tract. This is advantageous since it may be difficult or undesirable to modify certain portion of the gastro-intestinal tract. Therefore, by using a covering element 604, additional portion of the gastro-intestinal tract may be treated without modification. Alternatively, the covering element 601 may be disposed within the elongate element 601, such that the covering element 604 covers the substantially entire length of the elongate element 601, or a portion of the elongate element 601.

The covering element 604 may be constructed of material to maintain a patent identity and to reduce resistance, thereby allowing the under-digested nutrients to travel through the device substantially unhindered. The elongate element 601 may be constructed of a compliant material for optimized contact to the gastro-intestinal tract to minimize irritation or tissue damage.

Furthermore, it is contemplated that the covering element 604 may be constructed of elastic material, rigid material, or a combination thereof. For example, a portion of the covering element 604 disposed within the elongate element 601 may be constructed of rigid material and a portion of the covering element 604 disposed outside of elongate element 601 may be constructed of elastic material.

Figure 9A:
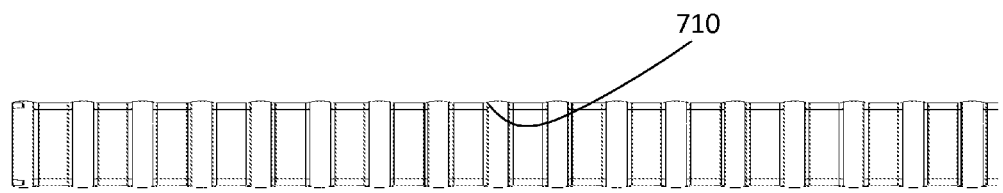
FIGS. 9A-9C illustrate one embodiment of the device comprising a multilayered elongate element.
Figure 9B:
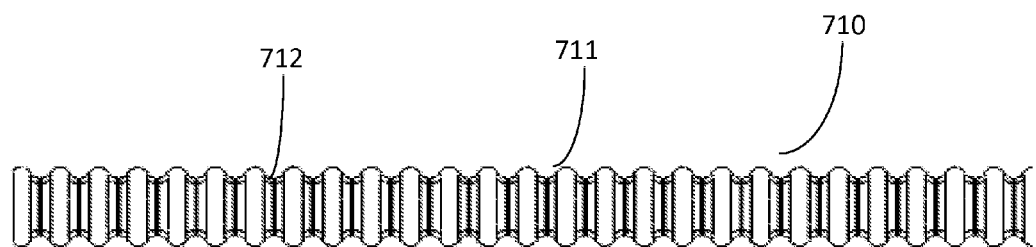
Figure 9C:
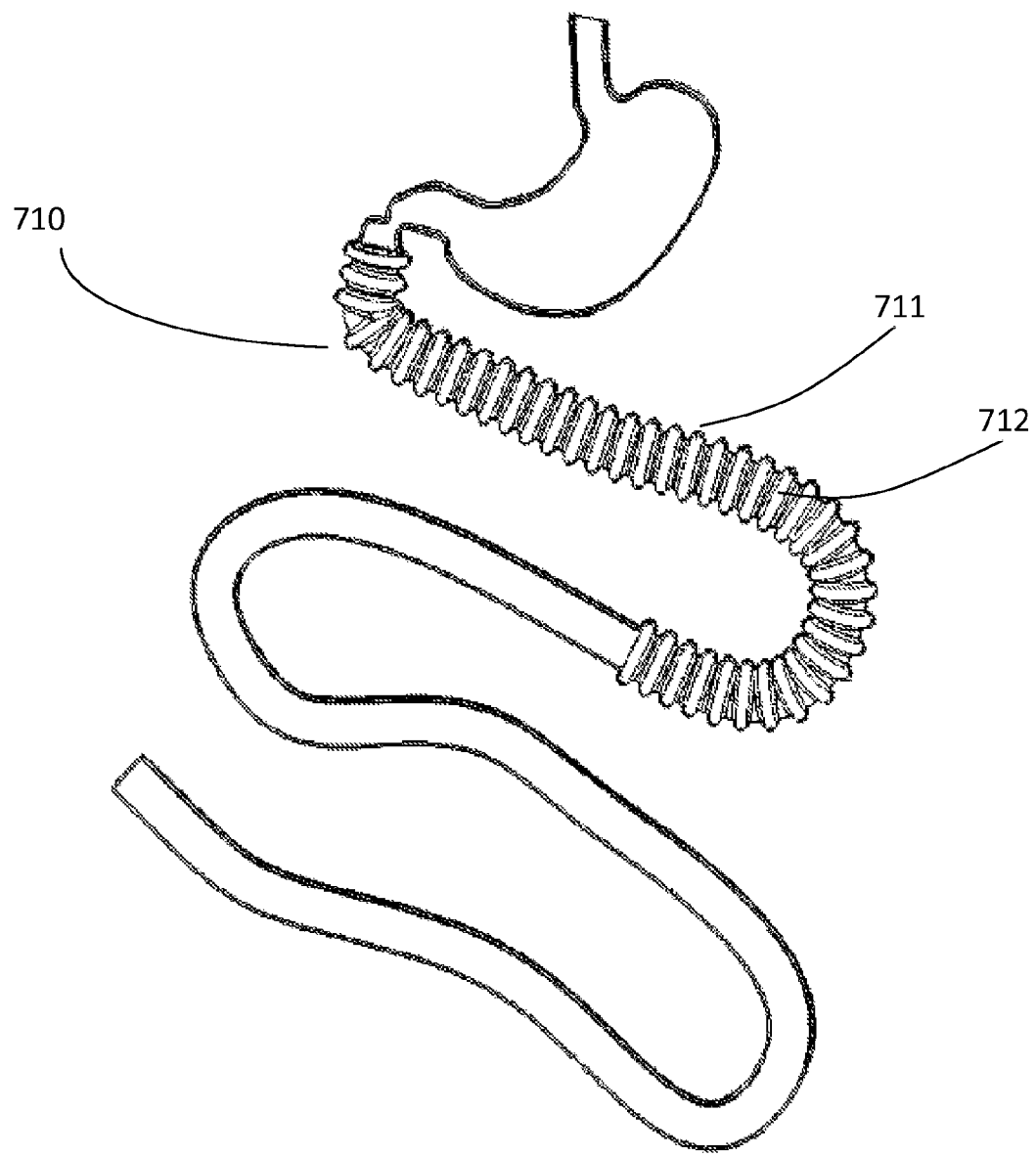

Referring now to FIGS. 9A-C, where a device comprising a multi-layered elongate element 710 is exemplarily shown. The elongate element 710 comprises a first layer and a second layer with a space configured to receive a fluid disposed in-between. The elongate element 710 is configured expand when the space is filled with a fluid (as seen in FIG. 9A) and contract when the fluid is removed (as seen in FIGS. 9B-9C).

The elongate element 710 filled with a fluid is inserted into the gastro-intestinal tract in its expanded form. Once the elongate element 710 is positioned over a portion of the gastro-intestinal tract to be modified, the fluid is removed such that a first portion of the elongate element 711 expands radially outwardly, whereas a second portion of the elongate element 712 contracts radially inwardly. The expansion of the portion 711 attaches the elongate element 710 to the gastro-intestinal tract, whereas the contraction of the second portion 712 reduces the length of the elongate element 700 and thus modifies the gastro-intestinal tract by compressing a portion thereof. Such embodiment is advantageous in that precise adjustment and readjustments are possible by controlling the amount of fluid into the elongate element 710.

Embodiments of the present disclosure further contemplate modifying a diameter of the gastro-intestinal tract. In one embodiment, a device constructed according to the principles of the present invention may increase the diameter of the gastro-intestinal tract. The increased gastro-intestinal diameter may increase the passage rate of the under-digested nutrients to the distal portion of the gastro-intestinal tract and enhances the release of hormones such as glp-1. In one embodiment, the device may comprise at least one attachment element as described above. The attachment element may be a substantially cylindrical structure with a body that defines an open space within the body. Generally, the attachment element is configured with a diameter larger than the diameter of a portion of the gastro-intestinal tract.

The attachment element may comprise one or more anchoring mechanisms to attach the attachment element to the gastro-intestinal tract as described above. Upon insertion into the gastro-intestinal tract, the anchoring mechanisms disposed on the attachment element attaches to the gastro-intestinal wall and thereby expanding the gastro-intestinal lumen radially and increase the diameter of the gastro-intestinal lumen. Alternatively, the attachment element may be self-expanding such as a radial stent. In such embodiment, the attachment element is inserted into the gastro-intestinal tract in a collapsed state, and upon insertion and placement, the attachment element is transformed into the expanded state thereby radially expanding the gastro-intestinal tract.

Furthermore, the attachment element may be adjustable such that the degree of radial expansion may be adjusted according to the anatomy and treatment needs of the subject. Additionally, a series of the attachment elements may be used to expand different portions of the gastro-intestinal tract. One or more elongate elements as described above may be disposed between to expand and cover a larger portion of the gastro-intestinal tract.

Alternatively, the device described above may be used to reduce the diameter of the gastro-intestinal tract such that the surface area of the gastro-intestinal tract that is in contact with under-digested nutrients is reduced.

Figure 10A:
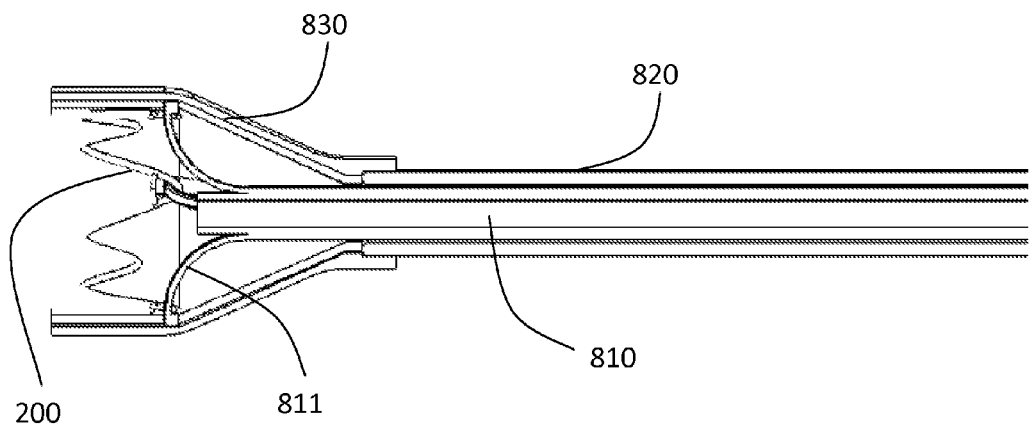
FIGS. 10A-10B illustrate exemplary loading and the delivery of the compression device into the patient.
Figure 10B:
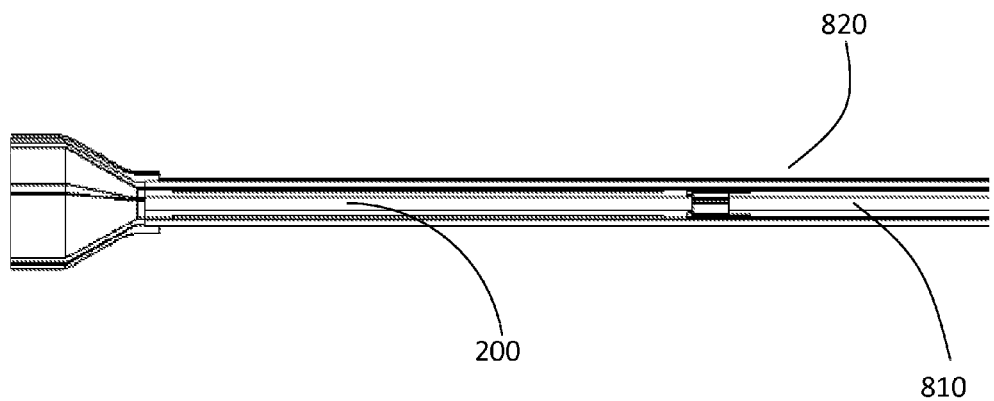

The device described above may be inserted into the body by utilizing a double catheter system. As seen in FIG. 10A, an exemplary compression device 200 comprising a self-expanding anchoring mechanism is loaded into the double catheter insertion system. The insertion system comprises an inner catheter 810 disposed within an outer catheter 820, and a detachable funnel element 830 wherein the apex of the funnel is connected to the outer catheter 820. The device is loaded into the insertion system by first inserting the first attachment element in its expanded configuration into the funnel element 830. Hook elements 811 disposed on the distal end of the inner catheter 810 then engages with and receives by the second attachment element. Thereafter, by pulling on the inner catheter 810 towards the proximal direction, the hook elements 811 guide the first attachment element towards the outer catheter 820 through the interior of the funnel element 830. While the first attachment element moves through the funnel element 830, the anchoring mechanism of the first attachment element is transformed into its collapsed state as the interior volume of the funnel element 830 decreases towards the outer catheter 820. Once the first attachment element is inserted into the outer catheter 820 in its collapsed state, the device 200 is further pulled towards the proximal direction until the entire device 200 is loaded into the outer catheter 830 in its collapsed state as seen in FIG. 10B.

During the insertion of device into the gastro-intestinal tract, the outer catheter 820 with the device 200 and the inner catheter 810 disposed within is inserted into a patient's body endoluminally. Upon reaching the attachment site, the second attachment element is deployed by pushing the inner catheter 810 towards the distal direction until the second attachment element exits the outer catheter 820. Upon exiting the outer catheter 520, the self expanding anchoring mechanism transforms from the collapsed state to the expanded state and thereby causing the second attachment element to engage the gastro-intestinal wall. Similarly, the first attachment element may be deployed as described above to complete the device delivery.

It is contemplated that various diagnostic imaging devices and methods such as computed tomography or optical imaging may be utilized to prior to or during insertion to determine the location of the attachment sites, the length and/or the diameter of the gastro-intestinal tract to be modified. For example, magnetic navigation or fluoroscopy may be used to determine the attachment sites. It is further contemplated that various diagnostic imaging devices and methods may be employed to monitor treatment progress. Additionally, at least a portion of the device may be constructed of transparent or translucent materials to allow visual inspection of the treatment region.

The present device may be utilized to restructure the gastro-intestinal tissue such that the gastro-intestinal tract substantially permanently assumes the compressed configuration after the removal of the device. In one embodiment, the tissue may be restructured by implanting the present device constructed of bioabsorbable material such that the device is absorbed into the tissue and the tissue retains the compressed configuration. Alternatively, the present device may be implanted within the gastro-intestinal tract for a period of time such that the gastro-intestinal tissue naturally assumes the compressed configuration after the present device is removed.

Additionally, it is contemplated that the gastro-intestinal tract may be compressed or otherwise modified for a period of time without implanting the present device. In one embodiment, a portion of the gastro-intestinal tract may be compressed by the present device or other methods. Then, the compressed portion may be maintained by utilizing sutures, adhesives, slips, staples, or any other means to maintain the compressed configuration.

Furthermore, it is contemplated that the gastro-intestinal tract may be compressed or otherwise modified by treating an external surface of the gastro-intestinal tract. The external surface of the gastro-intestinal tract may be accessed by methods such as laparoscopy or natural orifice endoscopic translumenal surgery. A device configured to modify the external surface may comprise sutures, adhesives, slips, staples, etc.

The various embodiments described above may be drug eluted to prevent and/or treatment infections or other tissues that may arise due to implantation. For example, the elongate element may be coated with a therapeutic drug such as antibiotic, anti-inflammatory agent, etc.

Although the present invention discloses devices and methods for treatment of Type-2 Diabetes and obesity, it is further contemplated that the embodiments of the present disclosure or variations thereof may be used to facilitate weight loss, treat gastro-intestinal ailments such as, gastrointestinal ulcers, tumors, etc. For example, the present device may be utilized to isolate and treat gastro-intestinal ulcers by attaching the first and the second attachment elements to a portion of the gastro-intestinal wall without compressing the gastro-intestinal tract, such that the device is implanted or localized within the gastro-intestinal tract.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A gastro-intestinal treatment device, comprising:
   an elongate element configured to extend within the gastro-intestinal tract;
   a first attachment element disposed on a first end of the elongate element configured to attach to the gastro-intestinal tract at a first position; and
   a second attachment element disposed on the distal a second end of the elongate element configured to attach to the gastro-intestinal tract at a second position;
   wherein the second attachment element is configured to cause at least a portion of the gastro-intestinal tract at the second position to be refracted towards the first position such that a region of the gastro-intestinal tract is compressed between the first and the second attachment elements and the effective length of the region of the gastro-intestinal tract is reduced;
   wherein at least one of the first attachment element or the second attachment element comprises at least one self-expanding anchoring mechanism comprising a self-expanding ring with one or more protrusions, wherein the protrusions of the self-expanding ring are configured to prevent the first or the second attachment elements from migrating from the position of attachment and
   wherein the device is configured to maintain the compression of the portion of the gastro-intestinal tract between the first and the second attachment elements.

2. The device of claim 1, further comprising a third attachment element disposed on the elongate element, wherein the third attachment element is configured to attach to the gastro-intestinal tract at a third position.

3. The device of claim 1, wherein the device is configured to expand a diameter of the gastro-intestinal tract.

4. The device of claim 1, wherein the device is configured to reduce a diameter of the gastro-intestinal tract.

5. The device of claim 1, further comprising a covering element, wherein at least a portion of the covering element is disposed within the elongate element.

6. The device of claim 5, wherein the covering element comprises biocompatible low friction material.

7. The device of claim 1, wherein the elongate element comprises biocompatible compliant material.

8. The device of claim 1, wherein the anchoring mechanism is a self expanding mechanism.

9. The device of claim 1, wherein the anchoring mechanism is a mechanical fastener.

10. The device of claim 1, wherein the anchoring mechanism is an inflatable balloon.

11. The device of claim 1, further comprising a tension element disposed within the elongate element.

12. The device of claim 11, wherein the tension element is a spring, a braid, or a net.

13. The device of claim 1, wherein the elongate element comprises one or more openings disposed on a surface of the elongate element.

14. The device of claim 1, wherein a degree of the compression of the gastro-intestinal tract is configured to be adjustable.

15. The device of claim 1, wherein the elongate element is configured to substantially cover the compressed portion of the gastro-intestinal tract.

16. A gastro-intestinal implantable device, comprising:
   an elongate element configured to extend within a portion of a gastro-intestinal tract;
   a first attachment element disposed on the elongate element configured to be implanted to the gastro-intestinal tract at a first position and a second attachment element disposed on the elongate element configured to be implanted to the gastro-intestinal tract at a second position,
   wherein the second attachment element is configured to cause a portion of the gastro-intestinal tract at the second position to be retracted towards the first position such that a region of the gastro-intestinal tract is compressed between the first and the second attachment elements,
   wherein at least one of the first attachment element or the second attachment element comprises at least one self-expanding anchoring mechanism comprising a self-expanding ring with one or more protrusions, wherein the protrusions of the self-expanding ring are configured to prevent the first or the second attachment elements from migrating from the position of attachment, and
   wherein the device is configured to maintain the compression of the portion of the gastro-intestinal tract between the first and the second attachment elements.

17. A tissue modification device, comprising:
   an elongate element configured to extend within a body region;
   a first attachment element disposed on4tae proximal end a first end of the elongate element configured to attach to the body region at a first position; and
   a second attachment element disposed on the distal end a second end of the elongate element configured to attach to the body region at a second position,
   wherein the second attachment element at the second position is configured to be moved towards the first position to compress at least a portion of the body region between the first attachment element and the second attachment element and wherein the compression modifies the tissue structure of the body portion
   wherein at least one of the first attachment element or the second attachment element comprises at least one self-expanding anchoring mechanism comprising a self-expanding ring with one or more protrusions, wherein the protrusions of the self-expanding ring are configured to prevent the first or the second attachment elements from migrating from the position of attachment, and
   wherein the device is configured to maintain the compression of the portion of the gastro-intestinal tract between the first and the second attachment elements.

* * * * *